United States Patent
Zhu et al.

(10) Patent No.: US 11,150,203 B2
(45) Date of Patent: Oct. 19, 2021

(54) DUAL-BEAM MULTIPHASE FLUID ANALYSIS SYSTEMS AND METHODS

(71) Applicant: Schlumberger Technology Corporation, Sugar Land, TX (US)

(72) Inventors: Jianhua Zhu, Singapore (SG); Charles Toussaint, Singapore (SG); Cheng-Gang Xie, Singapore (SG); Massimiliano Fiore, Singapore (SG); Alexander Vilstrup, Singapore (SG)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 24 days.

(21) Appl. No.: 16/275,379

(22) Filed: Feb. 14, 2019

(65) Prior Publication Data

US 2020/0264114 A1  Aug. 20, 2020

(51) Int. Cl.
| | |
|---|---|
| *G01N 23/12* | (2018.01) |
| *G01N 23/087* | (2018.01) |
| *G01N 33/28* | (2006.01) |
| *G01F 1/74* | (2006.01) |
| *G01F 1/44* | (2006.01) |

(52) U.S. Cl.
CPC .............. *G01N 23/12* (2013.01); *G01F 1/44* (2013.01); *G01F 1/74* (2013.01); *G01N 23/087* (2013.01); *G01N 33/2823* (2013.01); *G01N 33/2841* (2013.01); *G01N 33/2847* (2013.01); *G01N 2223/202* (2013.01); *G01N 2223/206* (2013.01)

(58) Field of Classification Search
CPC .. G01N 23/12; G01N 23/087; G01N 33/2823; G01N 33/2841; G01N 2223/206; G01N 2223/202; G01F 1/44; G01F 1/74
USPC .......................................................... 378/53
See application file for complete search history.

(56) References Cited

U.S. PATENT DOCUMENTS

| | | | |
|---|---|---|---|
| 5,689,540 A * | 11/1997 | Stephenson | G01N 23/22 378/53 |
| 6,776,054 B1 | 8/2004 | Stephenson et al. | |
| 7,684,540 B2 * | 3/2010 | Groves | G01N 33/2847 378/53 |

(Continued)

FOREIGN PATENT DOCUMENTS

WO  2014035275 A1  3/2014

OTHER PUBLICATIONS

G.A. Johansen, 2015, Gamma-ray tomography, in Industrial tomography: systems and applications, M Wang (Eds.) (Elsevier) Chapter 7, pp. 197-222.

(Continued)

*Primary Examiner* — Thomas R Artman

(57) ABSTRACT

A method for analyzing flow of a multiphase fluid through a flowmeter is provided. In one embodiment, the method includes transmitting two beams of electromagnetic radiation along different paths through a multiphase fluid and detecting the two transmitted beams with detectors. The method also includes determining a gas fraction and a water-in-liquid ratio of the multiphase fluid. The gas fraction is determined based on the detected first beam of electromagnetic radiation and the water-in-liquid ratio of the multiphase fluid is determined based on the detected second beam of electromagnetic radiation. Additional systems, devices, and methods are also disclosed.

22 Claims, 6 Drawing Sheets

(56) References Cited

U.S. PATENT DOCUMENTS

| | | | | |
|---|---|---|---|---|
| 7,903,782 B2* | 3/2011 | Groves | ............... | G01N 23/083 378/53 |
| 7,908,930 B2* | 3/2011 | Xie | ............... | G01F 1/74 73/861.04 |
| 8,525,534 B2 | 9/2013 | Brandt et al. | | |
| 9,581,558 B2* | 2/2017 | Cadalen | ............... | G01N 23/12 |
| 2007/0291898 A1* | 12/2007 | Groves | ............... | G01N 33/2841 378/51 |
| 2008/0319685 A1* | 12/2008 | Xie | ............... | G01F 1/712 702/45 |
| 2009/0161823 A1* | 6/2009 | Groves | ............... | G01N 33/2847 378/53 |
| 2009/0216463 A1* | 8/2009 | Xie | ............... | G01N 21/3554 702/24 |
| 2010/0164514 A1* | 7/2010 | Brandt | ............... | G01F 1/74 324/694 |
| 2010/0238445 A1* | 9/2010 | Roux | ............... | G16C 20/20 356/436 |
| 2012/0111124 A1* | 5/2012 | Hu | ............... | G01N 22/00 73/861.04 |
| 2012/0216625 A1 | 8/2012 | Bruno et al. | | |
| 2013/0034206 A1* | 2/2013 | Cadalen | ............... | G01N 23/12 378/51 |
| 2013/0282305 A1* | 10/2013 | Roux | ............... | G16C 20/20 702/28 |
| 2013/0319132 A1* | 12/2013 | Lupeau | ............... | G01N 33/2823 73/861.04 |
| 2013/0327154 A1* | 12/2013 | Xie | ............... | G01N 22/00 73/861.04 |
| 2014/0012507 A1* | 1/2014 | Trehan | ............... | G01N 33/2823 702/12 |
| 2014/0013857 A1* | 1/2014 | Lupeau | ............... | G01F 1/50 73/861.04 |
| 2014/0331783 A1* | 11/2014 | Xie | ............... | G01F 1/662 73/861.04 |
| 2014/0355737 A1* | 12/2014 | Korkin | ............... | G01F 1/34 378/53 |
| 2015/0136963 A1* | 5/2015 | Xie | ............... | G01N 21/8507 250/256 |
| 2015/0276447 A1* | 10/2015 | Black | ............... | G06T 11/00 702/48 |
| 2015/0316402 A1* | 11/2015 | Wee | ............... | G01F 1/363 73/861.04 |
| 2015/0377776 A1* | 12/2015 | Xie | ............... | G01N 21/3504 250/341.2 |
| 2016/0011033 A1* | 1/2016 | Chen | ............... | G01P 5/006 378/67 |
| 2016/0076925 A1* | 3/2016 | Chen | ............... | G01F 1/44 702/49 |
| 2016/0161425 A1* | 6/2016 | Berezin | ............... | G01N 22/00 324/638 |
| 2018/0274730 A1* | 9/2018 | Hollaender | ............... | G01N 33/2841 |
| 2018/0321068 A1* | 11/2018 | Meribout | ............... | G01F 1/712 |
| 2018/0348035 A1* | 12/2018 | Huang | ............... | G01F 15/00 |
| 2020/0264114 A1* | 8/2020 | Zhu | ............... | G01F 1/74 |

OTHER PUBLICATIONS

International Search Report and Written Opinion issued in the PCT application PCT/US2020/018094, dated May 21, 2020 (7 pages).

* cited by examiner

DUAL-BEAM MULTIPHASE FLUID ANALYSIS SYSTEMS AND METHODS

BACKGROUND

This disclosure relates to gas or oil well testing or production monitoring and, more particularly, to methods and apparatuses for analyzing multiphase fluids produced from gas or oil wells.

DESCRIPTION OF THE RELATED ART

Hydrocarbon fluids such as oil and natural gas are obtained from a subterranean geologic formation, referred to as a reservoir, by drilling a well that penetrates the hydrocarbon-bearing formation. Once a wellbore is drilled, the well may be tested for purposes of determining the reservoir productivity and other properties of the subterranean formation to assist in decision making for field development. Various components and equipment may be installed in order to monitor and conduct flow tests while producing the various fluids from the reservoir.

Well testing is done to provide reservoir characterization, estimation of well deliverability, evaluation of well completion and perforation strategy, and assess efficiency of performed operations on a well, such as drilling, completion, perforation, stimulation, etc. During a well test, one parameter obtained is the flow rate measured at the surface. Various types of analysis may be performed on the results of the flow tests to determine formation, fluid, and flow characteristics, such as on the data measured using flowmeters. Wells often produce a combination of water, oil and gas, making flow rate measurements rather complex.

One conventional way of measuring the flow rate is by separating fluid phases in a multiphase flow and then measuring the individual phases with single phase flowmeters. Separation into and measuring of single-phase flows are generally considered accurate. Although single-phase flow measurements are generally trustworthy, a difficulty arises when separation of the fluids is incomplete, thus providing a mixture of fluid phases (e.g., gas bubbles in oil) to be measured by a single-phase flowmeter and inaccurate results. Another potential drawback is that some information about the dynamic behavior of the fluid flow in the production well may be missed, as fluid flow rate is measured after separation. Consequently, the desire arose to measure the multiphase flow rate inline and in real time without separation using a multiphase flowmeter.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment of the present disclosure, a method includes receiving a multiphase fluid within a bore of a conduit and passing electromagnetic radiation with multiple energy levels through the multiphase fluid within the bore. Passing electromagnetic radiation through the multiphase fluid within the bore of the conduit includes transmitting a first beam of electromagnetic radiation through the multiphase fluid along a first beam path through the bore and transmitting a second beam of electromagnetic radiation through the multiphase fluid along a second beam path within the bore. The second beam path is different from the first beam path, and the first beam has a length within the bore along the first beam path greater than a length of the second beam within the bore along the second beam path. The method also includes detecting the first beam of electromagnetic radiation transmitted through the multiphase fluid at a first detector and detecting the second beam of electromagnetic radiation transmitted through the multiphase fluid at a second detector. Additionally, the method includes determining a gas fraction and a water-in-liquid ratio of the multiphase fluid within the bore. The gas fraction is determined based on the detected first beam of electromagnetic radiation and the water-in-liquid ratio of the multiphase fluid is determined based on the detected second beam of electromagnetic radiation.

In another embodiment of the present disclosure, a method includes receiving, within a bore of a conduit, a multiphase fluid that flows through the bore in an annular or annular-mist flow regime in which heavier fluid of the multiphase fluid forms a liquid film along an interior wall of the conduit defining the bore. The method also includes passing electromagnetic radiation with multiple energy levels through the multiphase fluid within the bore, which includes transmitting a first beam of electromagnetic radiation through the multiphase fluid along a first beam path through the bore and transmitting a second beam of electromagnetic radiation through the multiphase fluid along a second beam path within the bore. The second beam path is different from the first beam path, and the first beam has a length within the bore along the first beam path greater than a length of the second beam within the bore along the second beam path. The method further includes detecting the first beam of electromagnetic radiation transmitted through the multiphase fluid at a first detector, detecting the second beam of electromagnetic radiation transmitted through the multiphase fluid at a second detector, and determining a radius of a gas core of the multiphase fluid.

In an additional embodiment, an apparatus includes a fluid conduit having a bore and a measurement system positioned to emit multiple beams of electromagnetic radiation with multiple energy levels through a multiphase fluid received in the bore. The measurement system includes at least one radiation source, a first radiation detector positioned to receive a first beam emitted through the multiphase fluid along a first beam path from the at least one radiation source to the first radiation detector, and a second radiation detector positioned to receive a second beam emitted through the multiphase fluid along a second beam path from the at least one radiation source to the second radiation detector. The measurement system is arranged such that the first beam has a length within the bore along the first beam path greater than a length of the second beam within the bore along the second beam path. The measurement system also includes a computer to calculate a gas fraction of the multiphase fluid based on the first beam received by the first radiation detector and to calculate a water-in-liquid ratio of the multiphase fluid based on the second beam received by the second radiation detector.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

Certain embodiments of the disclosure will hereafter be described with reference to the drawings, wherein like reference numerals denote like elements. It should be understood, however, that the accompanying drawings illustrate just the various implementations described herein and are not meant to limit the scope of various technologies described herein. The drawings show and describe various embodiments of the current disclosure. More specifically.

DETAILED DESCRIPTION OF SPECIFIC EMBODIMENTS

Figure 1:
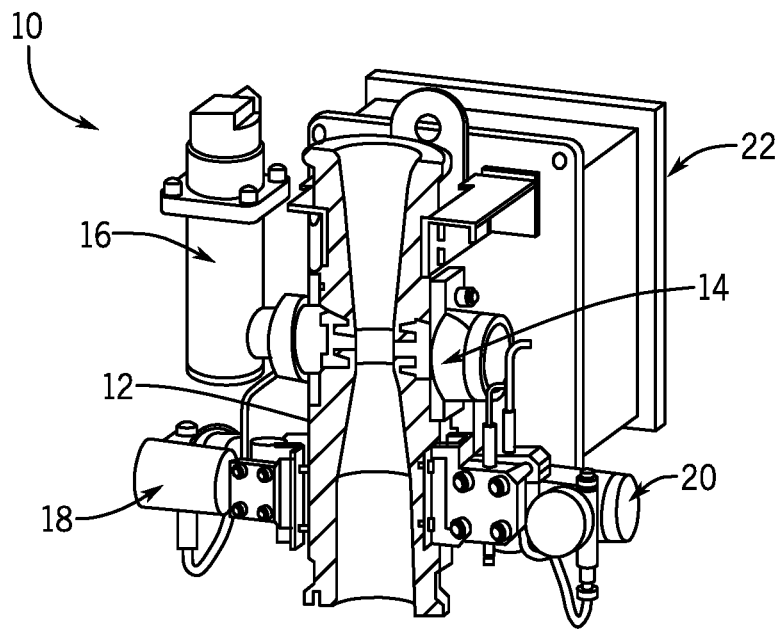
FIG. 1 generally depicts a flowmeter for analyzing a fluid in accordance with one embodiment of the present disclosure.

In the following description, numerous details are set forth to provide an understanding of the present disclosure. It will be understood by those skilled in the art, however, that the embodiments of the present disclosure may be practiced without these details and that numerous variations or modifications from the described embodiments may be possible.

In the specification and appended claims: the terms "connect," "connection," "connected," "in connection with," and "connecting" are used to mean "in direct connection with" or "in connection with via one or more elements," and the term "set" is used to mean "one element" or "more than one element." Further, the terms "couple," "coupling," "coupled," "coupled together," and "coupled with" are used to mean "directly coupled together" or "coupled together via one or more elements." As used herein, the terms "up" and "down"; "upper" and "lower"; "upwardly" and "downwardly"; "upstream" and "downstream"; "above" and "below"; and other like terms indicating relative positions above or below a given point or element are used in this description to more clearly describe some embodiments of the disclosure. When introducing elements of various embodiments, the articles "a," "an," "the," and "said" are intended to mean that there are one or more of the elements. The terms "comprising," "including," and "having" are intended to be inclusive and mean that there may be additional elements other than the listed elements.

Certain embodiments of the present disclosure generally relate to fluid analysis, such as fluid analysis of produced fluids during well production tests or permanent production monitoring. More particularly, some embodiments include a multiphase flowmeter designed to emit two beams of x-ray and/or gamma-ray electromagnetic radiation with multiple energies having different path-lengths through a fluid. In some examples, a first radiation beam is emitted along a diametrical path through a pipe section of a multiphase flow meter and a second radiation beam is emitted along a non-diametrical path through the pipe section. The first and second radiation beams may be emitted from the same radioactive multiple-energy source or from different radioactive sources with multiple energies.

In at least one embodiment, mixture density (gas/liquid fraction) determination can be made along the first diametrical beam at the highest energy level of the beam (such as at 356 keV for $^{133}$Ba source), where the effects of count-rate reduction along a large path-length is the smallest among the usable energy levels, and a water-in-liquid ratio (WLR) determination can be made along the second non-diametrical beam across the near-wall (liquid-rich) region at two or more lower energies of the second beam (such as at 32 keV and 81 keV for $^{133}$Ba source), where there is less reduction in count-rates measured along a smaller path-length. In some instances, such as during annular or annular-mist flow regimes presenting a concentric gas-core and liquid-annulus shape, two x-ray and/or gamma-ray radiation beams emitted along diametrical and non-diametrical paths through the fluid could also or instead be used to determine one or more of liquid film thickness, gas core radius, liquid fraction in the gas core, and water, gas, and oil fractions. In at least some instances, the present techniques may enhance measurement accuracy and facilitate measurement of high production flowrate in large diameter pipes over a wide range of gas volume fractions.

Turning now to the drawings, an apparatus 10 for analyzing fluid is generally depicted in FIG. 1 in accordance with one embodiment. While certain elements of the apparatus 10 are depicted in this figure and generally discussed below, it will be appreciated that the apparatus 10 may include other components in addition to, or in place of, those presently illustrated and discussed. Moreover, while the apparatus 10 may be provided in the form of a flowmeter (e.g., a multiphase flowmeter) as shown here and described below in connection with certain embodiments, the apparatus 10 could be provided in other forms as well. Further, in at least some instances the apparatus 10 is used to analyze fluids drawn from subterranean formations. Such analysis could be performed on fluids by the apparatus 10 subsea or at the surface.

As depicted, the apparatus includes a fluid conduit 12 for receiving a fluid to be analyzed and various sensors coupled to the fluid conduit 12 for measuring a characteristic of the fluid in the conduit 12. In the presently depicted embodiment, the sensors include a radiation detector 16 (which receives radiation from an emitter 14), a pressure transmitter 18, and a differential-pressure transmitter 20. A multi-variable transmitter (MVT) for pressure, temperature, and differential-pressure may be used to reduce flowmeter cost. The emitter 14 can emit electromagnetic radiation into the fluid, at least some of which is received by the radiation detector 16. In at least one embodiment, the emitter 14 includes a nuclear source (e.g., $^{133}$Ba) that emits nuclear radiation through the fluid to the radiation detector 16. In a different embodiment, the emitter 14 may also or instead include an x-ray generator that emits x-ray radiation with multiple energy levels through the fluid to the radiation detector 16. In other embodiments, the apparatus 10 includes multiple radiation detectors 16 positioned to receive nuclear or x-ray generator radiation emitted through the fluid by one or more emitters 14 having nuclear or x-ray generator sources. When multiple emitters 14 are used, each of the emitters 14 may include the same type of nuclear source (e.g., $^{133}$Ba) or x-ray generator source or one of the emitters 14 may have a different type of nuclear or x-ray generator source than another.

To facilitate certain measurements, such as flow rate, the fluid conduit 12 may be provided as a vertical Venturi section having a tapered bore and a Venturi throat to constrict fluid flow, as shown in FIG. 1. This constriction creates a pressure drop, which can be measured with the differential-pressure transmitter 20. Further, in at least one embodiment the emitter 14 and detector 16 are positioned about a Venturi throat (e.g., within the same transverse cross-section) in the fluid conduit 12 such that the detector 16 receives radiation that has been transmitted through fluid within the Venturi throat.

In some embodiments, the apparatus 10 is a multiphase flowmeter that uses radiation at two or more different energy levels or wavelengths. As one example, the apparatus 10 may use gamma or x-ray radiation (e.g., emitted across the Venturi throat) at two or more different energy levels. The attenuations of the x- and/or gamma-ray radiation at different energies may be measured and used to determine individual phase fractions of oil, gas, and water in a multiphase fluid routed through the flowmeter. The individual phase fractions and the Venturi differential pressure can be used to determine other fluid characteristics, such as mixture density, WLR, and mass flow rate.

The diameter of the Venturi throat may vary between different embodiments. For example, for the same Venturi throat/inlet diameter ratio of 0.5, smaller diameter throats may be used for some lower flow rates and fluids while a larger diameter throat may be desired for certain fluids at higher flow rates (e.g., for very high-rate oil/gas wells). In at least some embodiments, the Venturi throat of the fluid conduit 12 has an inner diameter of 60-150 millimeters (e.g., 65 mm or 88 mm). Increasing the throat diameter, however, can also increase transmission attenuation (leading to reduced photon count rates, particularly at lower gamma-ray or x-ray energies), such as when brine salinity of the fluid is high (e.g., during a full-water calibration of the apparatus 10) or when water fraction is intermittently high (e.g., during flows with high-WLR liquid slugs).

The apparatus 10 also includes a computer 22 (which may also be referred to as a controller or a control unit) for determining characteristics of fluid within the fluid conduit 12. In at least some embodiments, the computer 22 is provided in the form of a flow computer coupled with the other depicted components in a single unit to facilitate installation of a flowmeter in a larger system (e.g., an oilfield apparatus). More specifically, the computer 22 is operable to determine characteristics of fluids within the fluid conduit 12 from measurements collected by the other components, such as photon count rates from one or more detectors 16. For example, the computer 22 can determine, from Venturi differential pressure and mixture density, total flow rate of the fluid. Further, a computer 22 of a multiphase flowmeter can determine attenuations by the fluid at various energy levels of radiation by comparing the amount of radiation at the various energy levels emitted from the emitter 14 to the portion of such radiation actually received by the detector 16. The computer 22 can also use this information to calculate phase fractions (e.g., proportions of oil, gas, and water) and mixture density for a multiphase fluid within the fluid conduit 12. Individual-phase flow rates can be determined by combining the phase fraction measurements together with the total flow rate measurement. In some embodiments the computer 22 calculates a gas fraction of the multiphase fluid based on a first beam of x- and/or gamma-ray electromagnetic radiation and a WLR of the multiphase fluid based on a second beam of x- and/or gamma-ray electromagnetic radiation having a shorter path through the fluid than the first beam, as discussed further below. The computer 22 may also or instead calculate a radius of a gas core within an annular multiphase fluid, a liquid fraction of the gas core, a thickness of the annular liquid film surrounding the gas core, or a gas fraction of the multiphase fluid, such as also described below.

Figure 2:
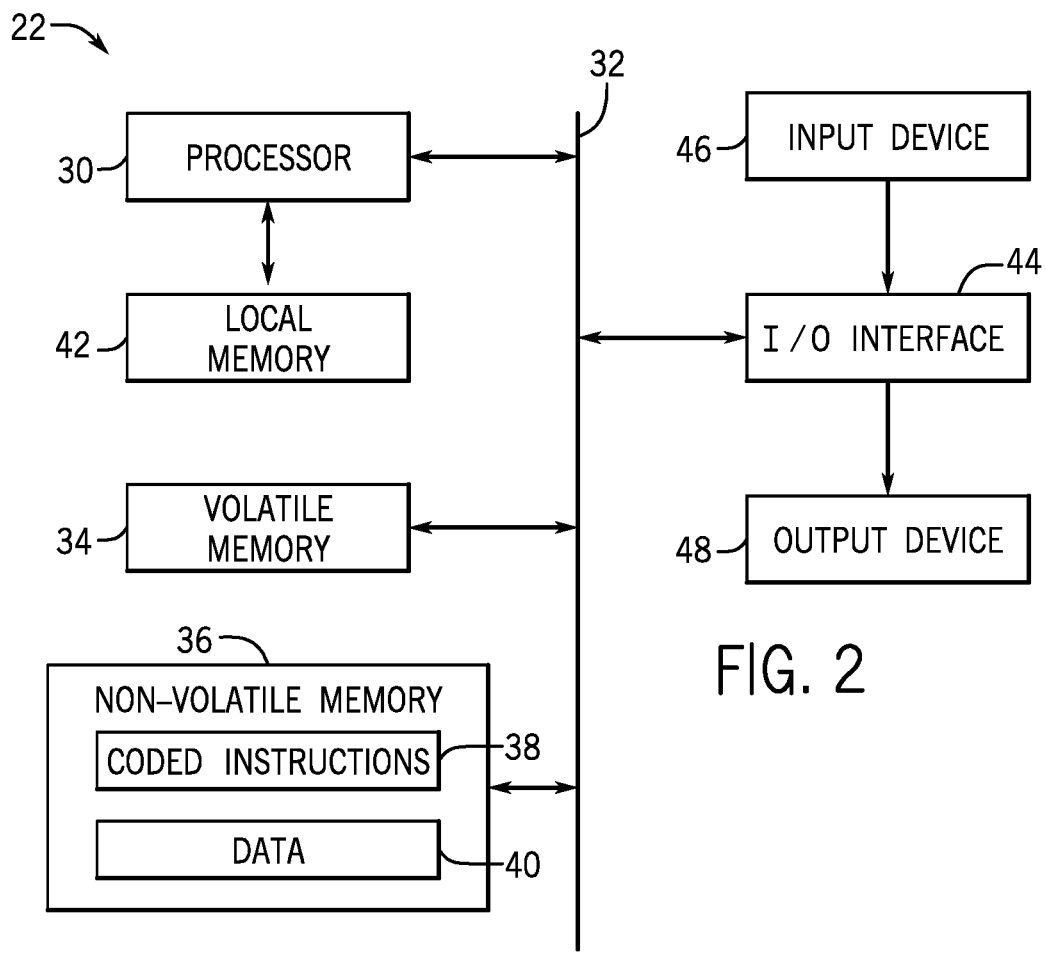
FIG. 2 is a block diagram of components of a computer of the flowmeter of FIG. 1 in accordance with one embodiment.

The computer 22 can be a processor-based system, an example of which is provided in FIG. 2. In this depicted embodiment, the computer 22 includes at least one processor 30 connected by a bus 32 to volatile memory 34 (e.g., random-access memory) and non-volatile memory 36 (e.g., flash memory and a read-only memory (ROM)). Coded application instructions 38 and data 40 are stored in the non-volatile memory 36. For example, the application instructions 38 can be stored in a ROM and the data 40 can be stored in a flash memory. The instructions 38 and the data 40 may be also be loaded into the volatile memory 34 (or in a local memory 42 of the processor) as desired, such as to reduce latency and increase operating efficiency of the computer 22. The coded application instructions 38 can be provided as software that may be executed by the processor 30 to enable various functionalities described herein. Non-limiting examples of these functionalities include determination of: incident photon count rates on a detector, radiation attenuation rates, phase fractions and mixture density for a multiphase fluid (oil, water, and gas fractions), flow rates, gas volume fraction (GVF), WLR, gas core radius, liquid fraction of a gas core, and liquid film thickness. In at least some embodiments, the application instructions 38 are encoded in a non-transitory computer readable storage medium, such as the volatile memory 34, the non-volatile memory 36, the local memory 42, or a portable storage device (e.g., a flash drive or a compact disc).

An interface 44 of the computer 22 enables communication between the processor 30 and various input devices 46 and output devices 48. The interface 44 can include any suitable device that enables such communication, such as a modem or a serial port. In some embodiments, the input devices 46 include one or more sensing components of the apparatus 10 (e.g., detector 16, pressure transmitter 18, and differential-pressure transmitter 20, or pressure/temperature/differential-pressure multi-variable transmitter (MVT)) and the output devices 48 include displays, printers, and storage devices that allow output of data received or generated by the computer 22. Input devices 46 and output devices 48 may be provided as part of the computer 22 or may be separately provided.

Further, while the computer 22 could be located with the fluid conduit 12 and sensing components of the apparatus 10 as a unitary system (e.g., a flowmeter), the computer 22 could also be located remote from the other components. Additionally, the computer 22 could be provided as a distributed system with a portion of the computer 22 located with the sensing components at the fluid conduit 12 and the remaining portion of the computer 22 located remote from the fluid conduit 12. One or more communication devices (e.g., of the interface 44) may facilitate wired or wireless communications of the multiphase-flowmeter measurement data (such as flow rates, WLR, GVF, or sensors' prognostic, diagnostic or quality-control information) to users' process-management systems, such as to a supervisory control and data acquisition (SCADA) system. A multiphase flowmeter may receive commands from a user through such a communication device to update multiphase flowmeter configuration or calibration settings. A plurality of multiphase flowmeters with connectivity may form part of the Industrial Internet of Things, to enable more efficient oil-gas reservoir management through big-data analytics and cloud computing.

As noted above, in at least some embodiments two radiation beams with multiple energy levels may be emitted through the fluid conduit 12 of a flowmeter 10 to facilitate analysis of a multiphase fluid. One example of this is provided in FIG. 3, which shows radiation beams 52 and 54 transmitted from an emitter 14 to detectors 16 along a cross-section of the conduit 12 through a bore 56 generally defined by a pipe wall 58 of the conduit 12. The emitter 14 of FIG. 3 includes a single multi-energy radioactive source 62, such as $^{133}$Ba, that emits electromagnetic radiation (e.g., x-rays and gamma-rays) of the beams 52 and 54. As will be appreciated, the emitter 14 can include collimating apertures designed to emit the beams 52 and 54 toward two radiation detectors 16 (i.e., a first detector 66 and a second detector 76).

In this depicted embodiment, the beam 52 is emitted along a diametrical path through the bore 56 and is received at a crystal 64 of the first detector 66 after passing through a window 68, the bore 56, a window 70, and a collimator 72. The beam 54 is instead emitted along a non-diametrical path through the bore 56 and is received at a crystal 74 of the second detector 76 after passing through the window 68, the bore 56, a window 80, and a collimator 82. The detector crystals 64 and 74 may be yttrium-aluminum-perovskite (YAP) crystals or some other suitable material. The windows 68, 70, and 80 are provided as pressure-retaining, radiation-energy-transparent monolithic windows in at least some cases. Although the detectors 16 may be provided as scintillation detectors, other types of detectors 16 (e.g., solid state detectors) could also or instead be used in other embodiments.

Figure 3:
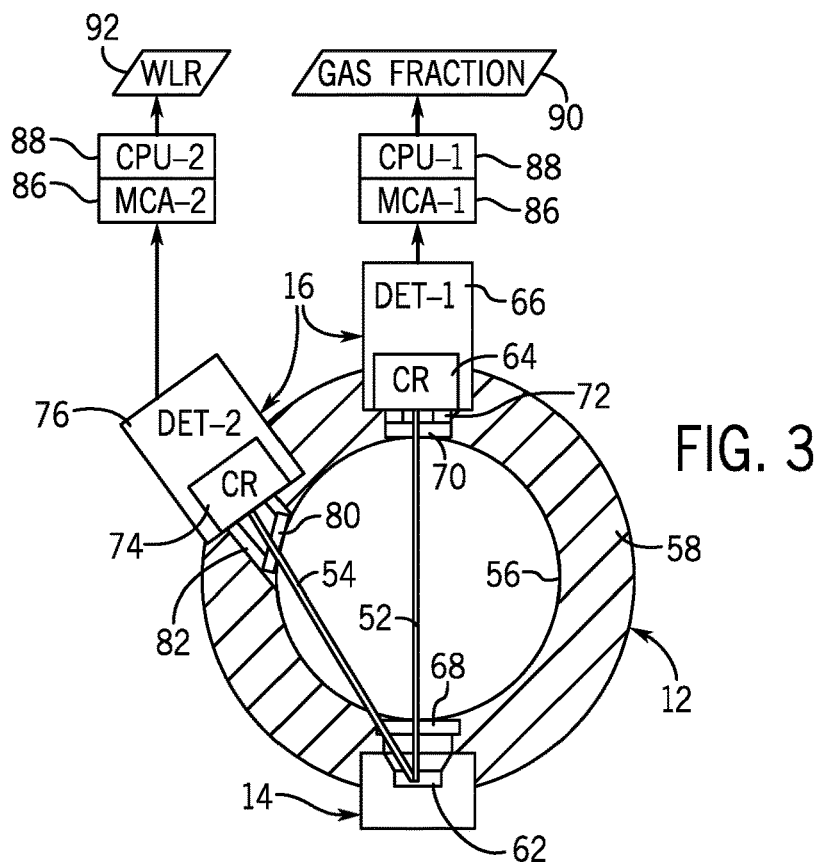
FIG. 3 is a cross-section of a conduit of a flowmeter using two radiation beams for analyzing a multiphase fluid within a bore of the conduit in accordance with one embodiment.

Because of their different beam paths, the second beam 54 has a shorter length within the bore 56 than does the first beam 52. That is, the distance traveled by the first beam 52 through a multiphase fluid within the bore 56 (i.e., between windows 68 and 70) is greater than the distance traveled by the second beam 54 through the multiphase fluid (i.e., between windows 68 and 80). The path length of the second beam 54 within the bore 56 may be seventy-five percent or less (or fifty-percent or less) than the path length of the first beam 52 within the bore 56 in some instances and may depend on the inner diameter of the bore 56. Although the beam 52 may be a diametrical beam, such as depicted in FIG. 3, the beam 52 could instead be a non-diametrical beam.

In at least some embodiments, a single high-energy measurement (such as at 356 keV for $^{133}$Ba source) is made by detector 66 (DET-1) along the first beam 52 for determining a gas fraction 90 (i.e., gas holdup) or mixture density, and two or more low-energy measurements (such as at 32 keV and 81 keV for $^{133}$Ba source) are made by detector 76 (DET-2) along the second beam 54 for determining a WLR 92 or liquid density. The low-energy measurements made along the second beam 54 could also be used to calculate a second gas fraction or a second mixture density to cross compare with the gas fraction or the mixture density measured along the first beam 52 in order to check the level of flow inhomogeneity to improve overall measurement accuracy. Two multi-channel analyzers (MCAs) 86 and central processing units (CPUs) 88 (e.g., of the computer 22) may be used with the detectors 66 and 76 to perform parallel gas fraction (mixture density) and WLR determinations. The energy levels at which the high-energy and low-energy measurements are taken may vary between embodiments of radioactive or x-ray generator sources. In at least one embodiment, a high-energy measurement is a count rate of gamma-ray photons at an energy level within an upper half (i.e., at or above a median) of the discrete gamma emission levels of a radioactive source 62 used and a low-energy measurement is a count rate of gamma-ray or x-ray photons at energy levels below the median of the discrete gamma emission levels of the source 62. In some embodiments, the high-energy measurement is a count rate of x-ray and/or gamma-ray photons at an appropriate highest energy level of the emission levels of the radioactive or x-ray generator source 62 used and low-energy measurements are count rates of x-ray and/or gamma-ray photons at other appropriate energy levels of the emission levels of the source 62. Further, in some embodiments a high-energy measurement is a count rate of gamma-ray photons from a source 62 at an energy level for which the Compton scattering effect is the dominant x- or gamma-ray-matter interaction effect, while a low-energy measurement is a count rate of gamma-ray or x-ray photons from the source 62 at an energy level for which the photoelectric effect is the dominant x- or gamma-ray-matter interaction effect.

Figure 4:
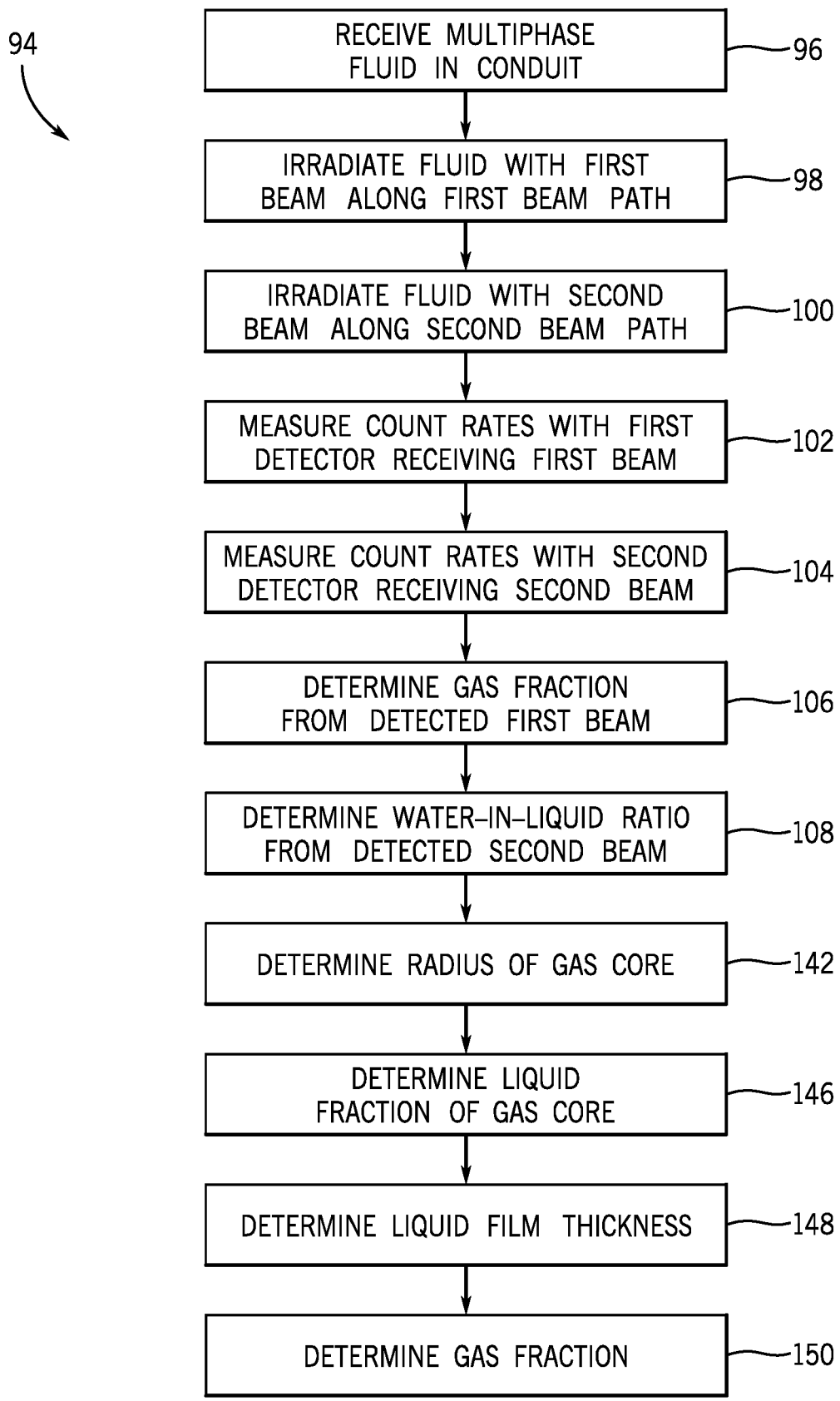
FIG. 4 is a flowchart for analyzing a multiphase fluid with two radiation beams to determine various characteristics of the multiphase fluid in accordance with one embodiment.

Turning now to FIG. 4, an example of a process for analyzing a multiphase fluid is generally represented by flowchart 94. In this embodiment, a multiphase fluid is received in a conduit (block 96), such as within the bore 56 of the conduit 12. The received multiphase fluid is then irradiated (e.g., at multiple energy levels) with a first beam (e.g., beam 52) of electromagnetic radiation (e.g., x- and/or gamma-ray radiation) along a first beam path (block 98) and a second beam (e.g., beam 54) of electromagnetic radiation (e.g., x- and/or gamma-ray radiation) along a second beam path (block 100). The first beam path can have a greater length within the multiphase fluid than the second beam path, such as described above. Additionally, in at least some embodiments the first beam path is a diametrical beam path through the bore 56 while the second beam path is a non-diametrical beam path through the bore 56.

A first detector (e.g., detector 66) receiving the first beam measures photon count rates for one or more energy levels (e.g., one of the highest energy levels) of the first beam (block 102). Similarly, a second detector (e.g., detector 76) receiving the second beam measures photon count rates for one or more energy levels (e.g., two or more low energy levels) of the second beam (block 104). The gas fraction 90 of the multiphase fluid is determined based on the detected first beam (block 106), such as from count rates of the first detector for the detected first beam, and the WLR 92 of the multiphase fluid is determined based on the detected second beam (block 108), such as from count rates of the second detector for the detected second beam.

Mixture density or gas fraction 90 can be determined from the count rate measured along the first beam 52 for the highest energy (such as at 356 keV for $^{133}$Ba source) photons in the beam 52, where the effects of count-rate reduction along a large path-length is the smallest. A full-spectra deconvolution for the highest energy count-rate measurement may be avoidable due to the absence of the undesirable effects (such as escape scattered gamma-ray Compton continuum) present in the low-energy spectra range and, consequently, a simpler photon-detection scheme may be used. In some embodiments, the detector 66 receiving the first beam 52 (for gas/liquid fraction determination) could be optimized in terms of collimator diameter (such as increased to 15 mm compared to 10 mm from some other designs) and/or scintillation YAP crystal length (such as increased to 15 mm from 10 mm) for desired count-rate measurement at the highest (largely composition-independent) energy across full-pipe water/brine (i.e., when the conduit 12 is filled with water/brine). Gas volume fraction (GVF) used for gas-liquid flow rate split can be derived from the determined cross-diameter gas fraction at the Venturi throat by using a suitable gas-liquid velocity slip-model.

A WLR (hence liquid density) determination can be made along the second beam 54 having a shorter path length across a near-wall (liquid-rich, low-GVF) region at two or more lower energies (such as at 32 keV (x-ray photons) and 81 keV (gamma-ray photons) for $^{133}$Ba source and/or even lower such as 18 keV fluorescence x-ray mostly generated by a portion of the 32-keV photons interacting with a thin metal foil), where increased reduction in count-rates would be detrimental to the accuracy of phase-fraction measurement if made along the longer path length of the first beam 52 through the fluid. A photon-detection scheme (via detector 76) with full-spectra deconvolution may be used for the second beam 54 for the WLR determination. For high-GVF wet-gas of annular or annular-mist flow regimes, a non-diametrical second beam 54 would interrogate the liquid-rich (locally low-GVF) region near the pipe wall (e.g., a vertical pipe wall 58), which may provide more accurate WLR determination based on two (or more) energy count-rate measurements. The two (or more) energy count-rate measurements made along the non-diametrical second beam 54 may also be used to calculate a second gas fraction or a second mixture density to cross compare with the gas fraction or the mixture density measured along the first beam 52, in order to check the level of flow inhomogeneity to improve overall measurement accuracy.

Although one example of an apparatus having an emitter 14 and two detectors 16 for analysis of a multiphase fluid is depicted in FIG. 3 and described above, the apparatus may take other forms. In one embodiment depicted in FIG. 5, for example, the apparatus includes a multiplexer (MUX) 112 that facilitates analysis of the multiphase fluid with one MCA 86 and one CPU 88, rather than two of each as shown in FIG. 3. As described above, one or more single high-energy measurements may be made by detector 66 (DET-1) along the beam 52 for determining mixture-density, gas holdup, etc., while two or more low-energy measurements may be made by detector 76 (DET-2) along the beam 54 for determining WLR. The MUX 112 can be used to select one of the detectors 66 or 76 (DET-1 and DET-2) at a time, where a longer-duration (e.g., ten minutes) or more frequent (e.g., at ten- or fifteen-minute intervals) measurement could be made along gas-rich beam 52 for the detector 66 (DET-1) for determining the fast-varying gas-holdup (i.e., gas fraction) or mixture density, and a shorter-duration (e.g., five minutes) or less frequent (e.g., at one-hour intervals) measurement could be made along liquid-rich beam 54 for the detector 76 (DET-2) for determining the typically slow-varying WLR (at a low-GVF near-wall region). Those two-detector measurements could be made alternately and repetitively, with the measurement sequence and duration programmable under the control of the CPU 88 or other logic control device. The measurements could be made at a 45 Hz count-rate sampling rate or at any other suitable sampling rate.

Figure 5:
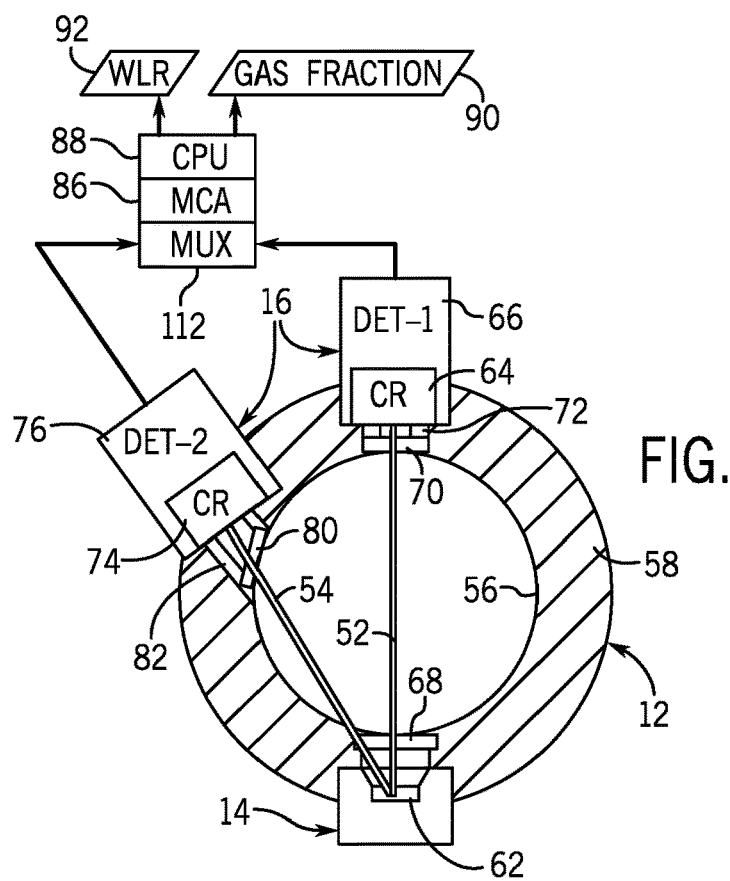
FIGS. 5-7 depict additional examples of flowmeters using two radiation beams for analyzing a multiphase fluid within a bore of a conduit in accordance with some embodiments.
Figure 6:
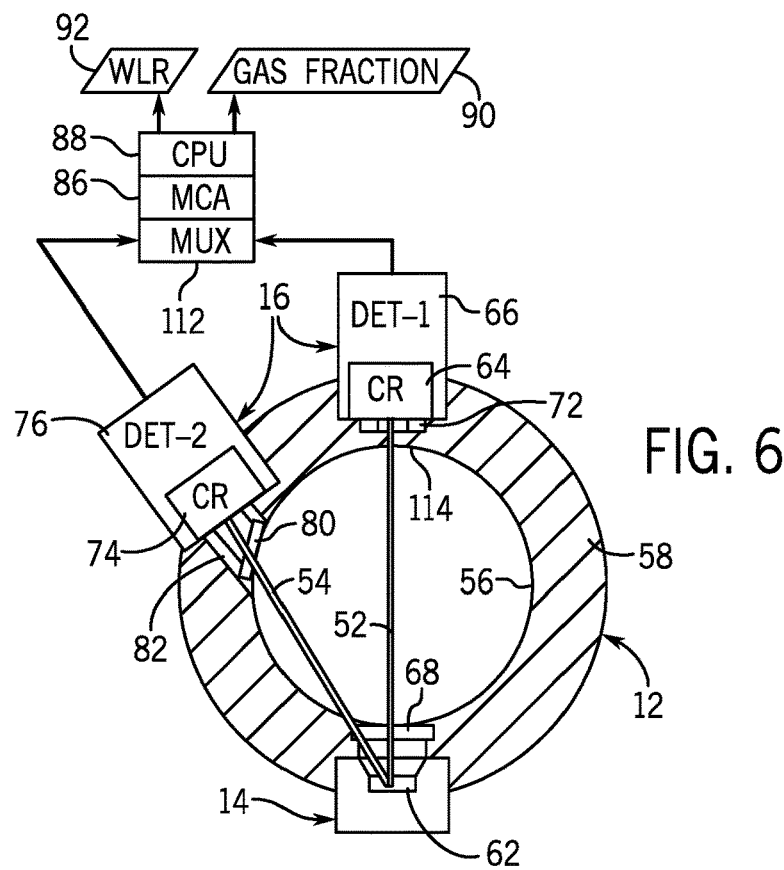

Another embodiment depicted in FIG. 6 differs from that of FIG. 5 in that the nuclear window 70 is omitted and the beam 52 is transmitted through a portion 114 of the pipe wall 58 (e.g., a metal pipe wall). The wall thickness at portion 114 may be designed so as to be sufficient to withstand design pressure, to have sufficient high-energy count rates, and to stop or filter low-energy photons of the beam 52 that are not used for the gas fraction or mixture density determination based on the beam 52.

Figure 7:
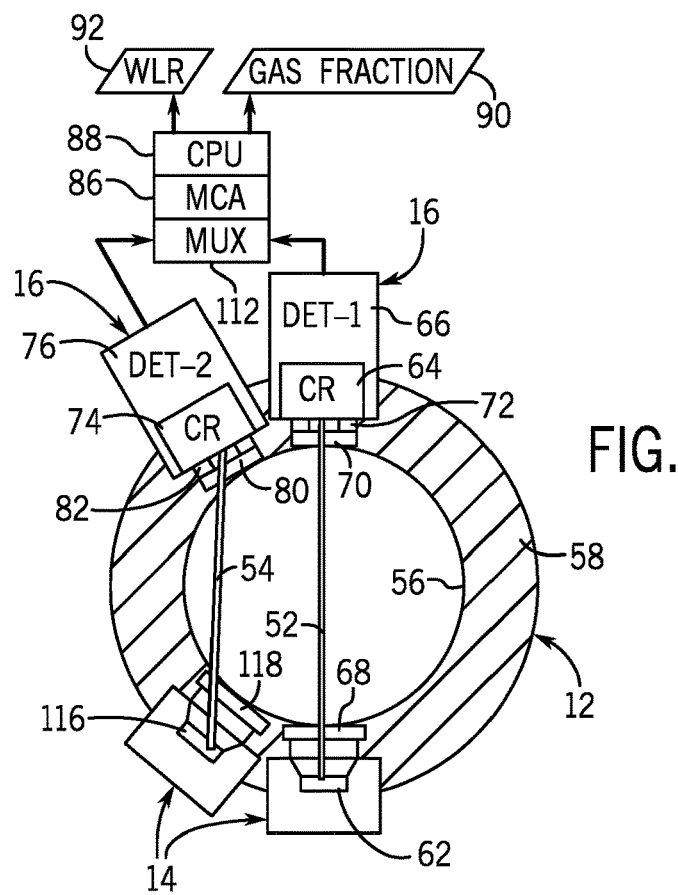

Although the beams 52 and 54 may be emitted from a shared multi-energy radioactive or x-ray generator source 62, in other embodiments these beams may be emitted from separate sources. As depicted in FIG. 7, for example, the first beam 52 is emitted from a single- or multi-energy radioactive or x-ray generator source 62, as described above, but the second beam 54 is instead emitted from a multi-energy radioactive or x-ray generator source 116 of a second emitter 14. This second beam 54 is transmitted to the detector 76 through a window 118, the bore 56, and the window 80. In some instances, the emitters 14 and detectors 16 may be arranged such that the paths of the beams 52 and 54 are parallel within a cross-section of the conduit 12. In some instances, the either or both of the emitter window 68 and the detector window 72 of FIG. 7 may be omitted for permitting high-energy measurement along the diametrical beam 52 through metal pipe walls.

Moreover, while the gas fraction and WLR of a multiphase fluid may be determined (e.g., blocks 106 and 108 of FIG. 4), other characteristics of the multiphase fluid may also or instead be determined. For wet-gas applications, for example, non-diametrical beam and diametrical-beam measurements can be combined to determine additional fluid characteristics or improve flow property measurement accuracy. In some embodiments, a diametrical beam 52 and a non-diametrical beam 54 such as described above may be emitted through a multiphase fluid having a three-phase flow with a concentric gas-core and liquid-annulus structure, such as annular, annular-mist, or mist flow, to determine various fluid properties. These determined fluid properties can include gas core radius (block 142 of FIG. 4), liquid fraction in the gas core (block 146), liquid film thickness (block 148), overall gas fraction (block 150), WLR, and water and oil fractions. The two beams 52 and 54 can be emitted from one multi-energy source (e.g., from source 62 through two collimating apertures) or from two different sources.

It will be appreciated that the fractions of each phase (i.e., gas, water, and oil) in a multiphase flow within a conduit can be measured by a single-beam dual-energy gamma ray. However, this would provide fractions in the area covered by the largely collimated beam, which may not be equal to the desired fractions over the conduit's cross section. This may especially be the case for a flow structure of core-and-annulus shape, where gas tends to concentrate in the core and liquid in the annulus; the gas fraction tends to be overestimated by cross-diameter single-beam measurement.

Certain embodiments of the present technique, however, use two radiation beams 52 and 54, which may improve the phase-fraction accuracy for core-annular flow structures, such as annular flow, annular-mist flow and mist flow that are prevalent for wet-gas flows. In at least some embodiments, the beam 52 is transmitted across a diameter of a circular bore 56 of a conduit 12 and the other beam 54 is off the diameter to pass closer to the wall 58 of the conduit 12. With this measurement configuration, two sets of equations of phase fractions of annular-type flows can be derived for calculating the above-said properties. Additionally, the liquid (annulus) film thickness and gas-core liquid fraction can be used in multiphase fluid modeling, such as for Venturi discharge coefficient calculation, mixture density calculation, and velocity profile prediction. While such information may not be extracted from a single-beam fraction measurement, the presently described measurement technique with beams 52 and 54 could be used to provide gas-core radius (at block 142), gas-core liquid fraction (at block 146), liquid film thickness (at block 148), and the overall gas fraction (at block 150) in a core-and-annulus-shape flow.

Figure 8:
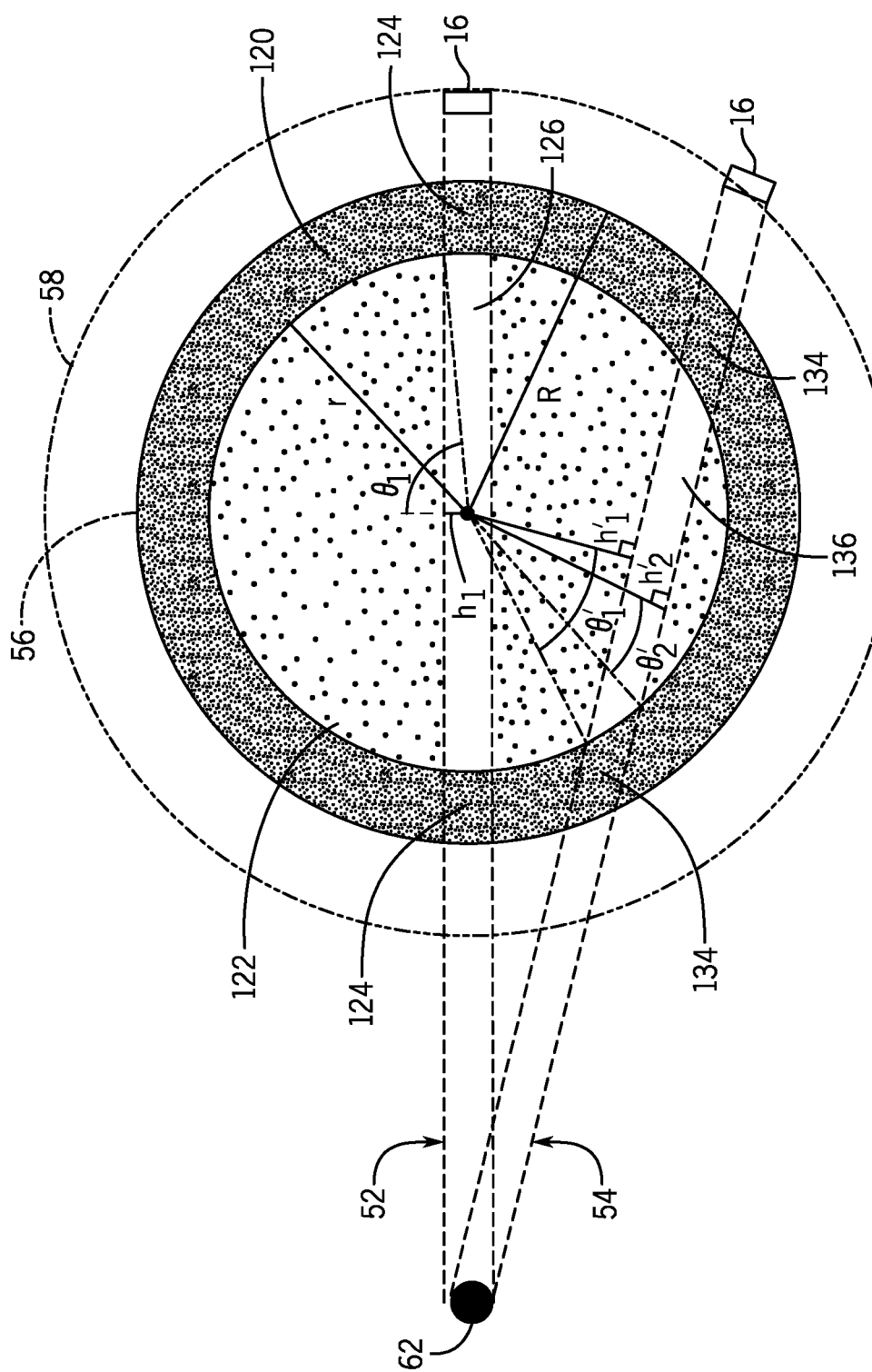
FIG. 8 is a cross-section of a conduit of a flowmeter using two radiation beams for analyzing a multiphase fluid having a liquid film surrounding a gas core in accordance with one embodiment.

An example of such a core-and-annulus flow of a multiphase fluid through the bore 56 of the conduit 12 is generally depicted in FIG. 8 as having a liquid film 120 surrounding a gas core 122. Although the liquid film 120 is predominantly liquid and the gas core 122 is predominantly gas, the liquid film 120 may include some gas (e.g., entrained bubbles) and the gas core 122 may include liquid (e.g., entrained droplets). In at least one embodiment, the liquid film 120 is assumed to be free of gas and the gas core 122 may be a mixture of gas and liquid of varying fractions in a cross-sectional area of the core. Two radiation beams 52 and 54 are transmitted through the multiphase fluid from the multi-energy radiation source 62, such as described above. The beam 52 can be a diametrical beam across the center of the bore 56 (e.g., across a Venturi throat of the conduit 12) and the beam 54 can be a non-diametrical beam.

Within the bore 56, the beam 52 crosses areas 124 of the liquid film 120 and an area 126 of the gas core 122, while the beam 54 crosses areas 134 of the liquid film 120 and an area 136 of the gas core 122. As shown in FIG. 8, the proportion of the path of beam 54 that traverses the liquid film 120 is greater than that of the path of the beam 52 that traverses the liquid film 120. In at least some embodiments, the beam crossed areas 126 and 136 of the gas core 122 and the total areas within the bore 56 crossed by the beam 52 (i.e., the sum of areas 124 and 126) and by the beam 54 (i.e., the sum of areas 134 and 136) can be used to calculate various characteristics of the analyzed multiphase fluid, such as a radius r of the gas core 122, liquid fraction in the gas core 122, thickness of the liquid film 120, WLR, and phase fractions within the bore 56 (of bore radius R, and r≤R).

For example, the beam crossed area 126 in the central core by the diametrical beam can be calculated as:

$$a_c = (\pi - 2\theta_1)r^2 + \sqrt{r^2 - h_1^2}\, h_1 \quad (1a)$$

and the beam crossed area 136 in the core by the off-diameter beam is:

$$a'_c = (\theta_1 - \theta_2)r^2 - \sqrt{r^2 - h'_1{}^2}\, h'_1 + \sqrt{r^2 - h'_2{}^2}\, h'_2 \quad (1b)$$

where $h_1$ is the perpendicular distance between the conduit center and the edge of the diametrical beam 52, $h'_1$ is the perpendicular distance between the conduit center and the upper edge of the off-diameter beam 54, and $h'_2$ is the perpendicular distance between the conduit center and the lower edge of beam 54 (which is colinear with $h'_1$ but shown offset in FIG. 8 for clarity). Further, R is the radius of the bore 56, r is the radius of the central core (which is initially unknown), $$\theta_1 = \cos^{-1}\frac{h_1}{r},$$

$$\theta'_1 = \cos^{-1}\frac{h'_1}{r} \text{ and }$$

$$\theta'_2 = \cos^{-1}\frac{h'_2}{r}.$$

It may be assumed that gas and liquid droplets are mixed homogenously in the central core 122 with core liquid fraction being $\widetilde{\alpha_{liq}}$ with respect to the core cross sectional area, and the gamma-ray measured liquid fractions are $\Gamma_{liq}$ and $\Gamma'_{liq}$ for the diametrical beam 52 and off-diameter beam 54, respectively. The measured gas fractions are therefore $\Gamma_{gas} = 1 - \Gamma_{liq}$ and $\Gamma'_{gas} = 1 - \Gamma'_{liq}$. Further:

$$\Gamma_{liq} = \frac{\widetilde{\alpha_{liq}} a_c + (a - a_c)}{a} \quad (2a)$$

$$\Gamma'_{liq} = \frac{\widetilde{\alpha_{liq}} a'_c + (a' - a'_c)}{a'} \quad (2b)$$

where a is the beam crossed area (areas 124 and 126) by the diametrical beam 52, and a' is that (areas 134 and 136) by the off-diameter beam 54. It is noted that a and a' are constants that depend on the beam geometries. Substituting equation 1 to equation 2 and reorganizing 2a and 2b to eliminate $\widetilde{\alpha_{liq}}$ gives:

$$\left[\Gamma'_{gas} a'\left(\pi - 2\cos^{-1}\frac{h_1}{r}\right) - \Gamma_{gas} a\left(\cos^{-1}\frac{h'_1}{r} - \cos^{-1}\frac{h'_2}{r}\right)\right]r^2 + \quad (3)$$
$$2\Gamma'_{gas} a'\sqrt{r^2 - h_1^2}\, h_1 + 2\Gamma_{gas} a\left(\sqrt{r^2 - h'_1{}^2}\, h'_1 - \sqrt{r^2 - h'_2{}^2}\, h'_1\right) = 0$$

Equation 3 has a sole unknown variable r and can be solved using an iterative method, such as Newton's method, or any other suitable technique(s). After solving equation 3 for gas-core radius r, the film thickness can be calculated as:

$$t = R - r \quad (4a)$$

Liquid fraction in the core can be calculated as:

$$\widetilde{\alpha_{liq}} = \frac{a_c - \Gamma_{gas} a}{a_c} \quad (4b)$$

Gas fraction of the conduit cross section can be calculated as:

$$\alpha_g = \frac{r^2}{R^2}(1 - \widetilde{\alpha_{liq}}) = \frac{r^2}{R^2}\widetilde{\alpha_{gas}} \quad (4c)$$

The WLR can be determined by the use of dual-energy gamma-ray measurement(s) made using a diametrical beam (e.g., beam 52) and/or using an off-diameter (near-wall) beam (e.g., beam 54) that passes through a locally liquid-rich region (which may facilitate higher accuracy in wet-gas WLR measurement). For example, the WLR determined by the off-diameter beam is:

$$WLR = \frac{\Gamma'_{water}}{\Gamma'_{water} + \Gamma'_{oil}} = \frac{\Gamma'_{water}}{\Gamma'_{liq}} \quad (4d)$$

The water and oil fractions of the conduit cross section can then be calculated as:

$$\alpha_o = (1-WLR)(1-\alpha_g) \quad (4e)$$

$$\alpha_w = WLR(1-\alpha_g) \quad (4f)$$

Figure 9:
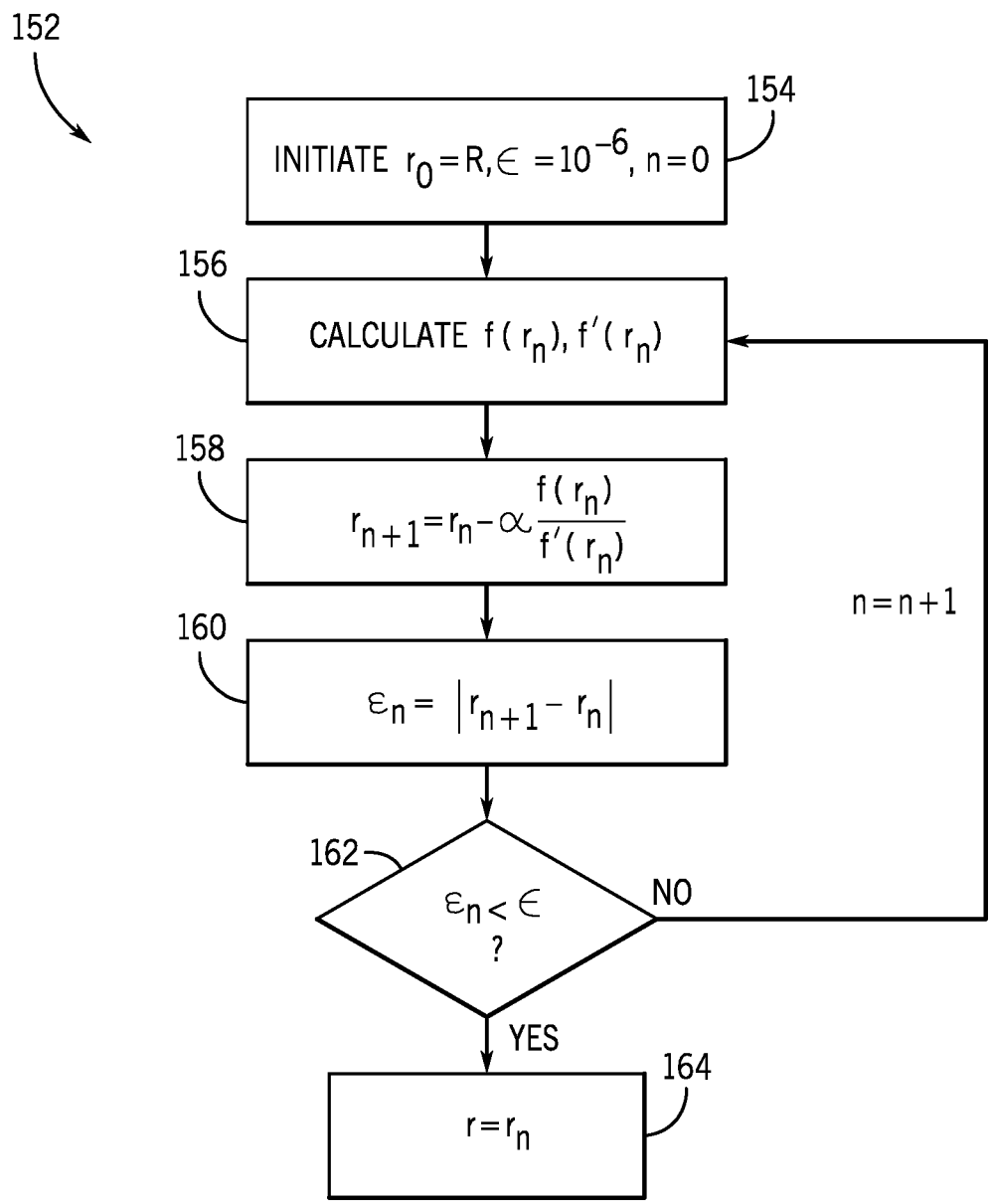
FIG. 9 is a flowchart for determining a radius of the gas core of FIG. 8 in accordance with one embodiment.

Assuming the left-hand side of equation 3 is function f(r), the flowchart 152 of FIG. 9 generally illustrates the use of Newton's algorithm to iteratively solve equation 3, where n is the iterative number, f'(r) is the first derivative of function f(r), $\in$ is the convergence criteria and $\alpha$ is the relaxation factor defined as $\alpha \in (0,1]$. After problem initialization (block 154), f(r) and f'(r) are calculated (block 156), a subsequent approximation is calculated (block 158), and the values of the current and immediately prior approximations are compared (block 160). If the absolute value of the difference of the current and prior approximations is below the convergence criteria (block 162), the method ends (block 164). Otherwise, the iterative number is incremented and blocks 156, 158, 160, and 162 may be repeated until the desired convergence criteria is met. It will be appreciated that other iterative algorithm(s) can also or instead be used to solve equation 3.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A method comprising:
   receiving a multiphase fluid within a bore of a conduit;
   passing electromagnetic radiation with multiple energy levels through the multiphase fluid within the bore of the conduit, wherein passing the electromagnetic radiation through the multiphase fluid within the bore of the conduit includes:
      transmitting a first beam of electromagnetic radiation through the multiphase fluid along a first beam path through the bore; and
      transmitting a second beam of electromagnetic radiation through the multiphase fluid along a second beam path within the bore that is different from the first beam path, wherein the first beam has a length within the bore along the first beam path greater than a length of the second beam within the bore along the second beam path;
   detecting the first beam of electromagnetic radiation transmitted through the multiphase fluid at a first detector;
   detecting the second beam of electromagnetic radiation transmitted through the multiphase fluid at a second detector; and
   determining a gas fraction and a water-in-liquid ratio of the multiphase fluid within the bore, wherein determining the gas fraction is based on the detected first beam of electromagnetic radiation and determining the water-in-liquid ratio of the multiphase fluid is based on the detected second beam of electromagnetic radiation;
   wherein determining the gas fraction is based on the detected first beam of electromagnetic radiation at a first energy level of the multiple energy levels and determining the water-in-liquid ratio of the multiphase fluid is based on the detected second beam of electromagnetic radiation at two or more energy levels of the multiple energy levels that are lower than that of the first energy level.

2. The method of claim 1, wherein transmitting the first beam of electromagnetic radiation through the multiphase fluid along the first beam path through the bore includes transmitting the first beam of electromagnetic radiation through the multiphase fluid along a diametrical beam path through the bore.

3. The method of claim 1, wherein the multiphase fluid flows through the bore in an annular or annular-mist flow regime in which heavier fluid of the multiphase fluid forms a liquid film along an interior wall of the conduit defining the bore, and passing electromagnetic radiation with multiple energy levels through the multiphase fluid within the bore of the conduit includes transmitting the first and second beams of electromagnetic radiation such that a proportion of the second beam path within the bore that traverses the liquid film along the interior wall is greater than a proportion of the first beam path within the bore that traverses the liquid film along the interior wall.

4. The method of claim 3, wherein transmitting the first beam of electromagnetic radiation through the multiphase fluid along the first beam path through the bore includes transmitting the first beam through a gas core of the multiphase fluid within the bore.

5. The method of claim 4, wherein determining the gas fraction based on the detected first beam of electromagnetic radiation includes determining the gas fraction based on photons of the first beam of electromagnetic radiation detected at the first detector having an energy level that is higher than energy levels of photons of the second beam of electromagnetic radiation detected at the second detector on which the determining of the water-in-liquid ratio is based.

6. The method of claim 5, wherein transmitting the first beam of electromagnetic radiation through the multiphase fluid along the first beam path through the bore includes emitting the first beam from a radioactive source having gamma emissions at discrete energy levels, and the photons of the first beam of electromagnetic radiation on which the gas fraction determining is based are gamma-ray photons within the upper half of the energy levels of the gamma emissions.

7. The method of claim 6, wherein transmitting the second beam of electromagnetic radiation through the multiphase fluid along the second beam path within the bore includes emitting the second beam from the same radioactive source from which the first beam is emitted.

8. The method of claim 7, wherein the photons of the second beam of electromagnetic radiation detected at the second detector on which the determining of the water-in-liquid ratio is based include gamma-ray photons within the lower half of the energy levels of the gamma emissions.

9. The method of claim 7, wherein the photons of the second beam of electromagnetic radiation detected at the second detector on which the determining of the water-in-liquid ratio is based include x-ray photons emitted from the radioactive source.

10. The method of claim 3, comprising determining a radius of a gas core of the multiphase fluid within the bore.

11. The method of claim 10, comprising determining a liquid fraction of the gas core of the multiphase fluid within the bore.

12. The method of claim 11, comprising determining the gas fraction of the multiphase fluid within the bore of the conduit based on the determined radius of the gas core and the determined liquid fraction of the gas core of the multiphase fluid within the bore.

13. The method of claim 1, wherein the multiphase fluid is not stratified.

14. A method comprising:
receiving a multiphase fluid within a bore of a conduit;
passing electromagnetic radiation with multiple energy levels through the multiphase fluid within the bore of the conduit, wherein the multiphase fluid flows through the bore in an annular or annular-mist flow regime in which heavier fluid of the multiphase fluid forms a liquid film along an interior wall of the conduit defining the bore, and passing electromagnetic radiation with multiple energy levels through the multiphase fluid within the bore of the conduit includes:
 transmitting a first beam of electromagnetic radiation through the multiphase fluid along a first beam path through the bore; and
 transmitting a second beam of electromagnetic radiation through the multiphase fluid along a second beam path within the bore that is different from the first beam path, wherein the first beam has a length within the bore along the first beam path greater than a length of the second beam within the bore along the second beam path;
detecting the first beam of electromagnetic radiation transmitted through the multiphase fluid at a first detector;
detecting the second beam of electromagnetic radiation transmitted through the multiphase fluid at a second detector; and
determining a radius of a gas core of the multiphase fluid within the bore based on the detected first beam of electromagnetic radiation and on the detected second beam of electromagnetic radiation.

15. The method of claim 14, comprising determining a liquid fraction of the gas core of the multiphase fluid within the bore.

16. The method of claim 15, comprising determining a gas fraction of the multiphase fluid within the bore of the conduit based on the determined radius of the gas core and the determined liquid fraction of the gas core of the multiphase fluid within the bore.

17. The method of claim 14, wherein the multiphase fluid is not stratified.

18. An apparatus comprising:
a fluid conduit including a bore; and
a measurement system positioned to emit multiple beams of electromagnetic radiation at multiple energy levels through a multiphase fluid received in the bore, the measurement system including:
 at least one radiation source;
 a first radiation detector positioned to receive a first beam, of the multiple beams, emitted through the multiphase fluid along a first beam path from the at least one radiation source to the first radiation detector;
 a second radiation detector positioned to receive a second beam, of the multiple beams, emitted through the multiphase fluid along a second beam path from the at least one radiation source to the second radiation detector, wherein the first beam has a length within the bore along the first beam path greater than a length of the second beam within the bore along the second beam path; and
 a computer encoded with instructions to calculate a gas fraction of the multiphase fluid based on the first beam received by the first radiation detector at a first energy level of the multiple energy levels and to calculate a water-in-liquid ratio of the multiphase fluid based on the second beam received by the second radiation detector at two or more energy levels of the multiple energy levels that are lower than that of the first energy level.

19. The apparatus of claim 18, wherein the at least one radiation source includes a Barium-133 isotope with multiple energy levels emitting at 32 keV x-rays and at 81 keV and 356 keV gamma-rays.

20. The apparatus of claim 18, wherein the at least one radiation source includes a multiple-energy x-ray generator.

21. The apparatus of claim 18, wherein the at least one radiation source, the first radiation detector, and the second radiation detector are located at the same transverse cross-section of a Venturi throat of the fluid conduit.

22. The apparatus of claim 18, wherein the multiphase fluid is not stratified.

* * * * *